(12) United States Patent
Ono

(10) Patent No.: US 9,750,402 B2
(45) Date of Patent: Sep. 5, 2017

(54) OPHTHALMOLOGIC APPARATUS, IMAGE PROCESSING METHOD, AND MEDIUM

(71) Applicant: CANON KABUSHIKI KAISHA, Tokyo (JP)

(72) Inventor: Mitsuhiro Ono, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/011,278

(22) Filed: Jan. 29, 2016

(65) Prior Publication Data

US 2016/0220108 A1 Aug. 4, 2016

(30) Foreign Application Priority Data

Jan. 30, 2015 (JP) ................. 2015-016745

(51) Int. Cl.
*A61B 3/14* (2006.01)
*A61B 3/10* (2006.01)
*A61B 3/00* (2006.01)
*G06T 5/00* (2006.01)
*A61B 3/12* (2006.01)

(52) U.S. Cl.
CPC .......... *A61B 3/0025* (2013.01); *A61B 3/1241* (2013.01); *A61B 3/14* (2013.01); *G06T 5/007* (2013.01); *G06T 2207/30041* (2013.01)

(58) Field of Classification Search
USPC ............................................... 351/200–246
See application file for complete search history.

(56) References Cited

U.S. PATENT DOCUMENTS

| 2011/0007271 | A1 | 1/2011 | Ono | |
| 2011/0267581 | A1* | 11/2011 | Nakajima | A61B 3/102 351/206 |
| 2012/0218515 | A1* | 8/2012 | Imamura | A61B 3/12 351/206 |
| 2013/0093995 | A1* | 4/2013 | Suehira | A61B 3/102 351/206 |
| 2014/0198300 | A1* | 7/2014 | Goto | G01B 9/0203 351/206 |

(Continued)

FOREIGN PATENT DOCUMENTS

JP 2003-310556 A 11/2003

OTHER PUBLICATIONS

Michael D. Abramoff, et al., "Retinal Imaging and Image Analysis", IEEE Reviews in Biomedical Engineering, vol. 3, 2010, pp. 169-208, Jan. 2010.

(Continued)

*Primary Examiner* — Mohammed Hasan
(74) *Attorney, Agent, or Firm* — Canon U.S.A., Inc. IP Division

(57) ABSTRACT

A disclosed ophthalmologic apparatus includes an image acquisition unit configured to acquire a fundus image of an eye to be examined on the basis of returning light from a fundus that is obtained by irradiating the fundus of the eye with light; and a correction unit configured to correct the fundus image in accordance with a degree of clouding of a clouded portion of the eye such that, among color components contained in the fundus image, a ratio of a color component, in the fundus image, that is scattered by a clouded portion of the eye at a higher rate increases against a ratio of another color component.

15 Claims, 9 Drawing Sheets

(56) References Cited

U.S. PATENT DOCUMENTS

2016/0157710 A1* 6/2016 Tomatsu .............. A61B 3/0025
351/206

OTHER PUBLICATIONS

Larry D. Hubbard, et al. "Brightness, Contrast, and Color Balance of Digital versus Film Retinal Images in the Age-Related Eye Disease Study 2", Investigative Ophthalmology & Visual Science, vol. 49, No. 8, pp. 3269-3282, Aug. 2008.
Timothy J. Bennett, "Monochromatic Fundus Photography", Ophthalmic Photographer's Society, pp. 1-6, Hershey PA., XP055279303, Jul. 2014.
Timothy J. Bennett, "Monochromatic Fundus Photography", Ophthalmic Photographer's Society, cleaner copy repaginated pp. 1-15, Hershey, PA., XP055279303, Jul. 2014.

* cited by examiner

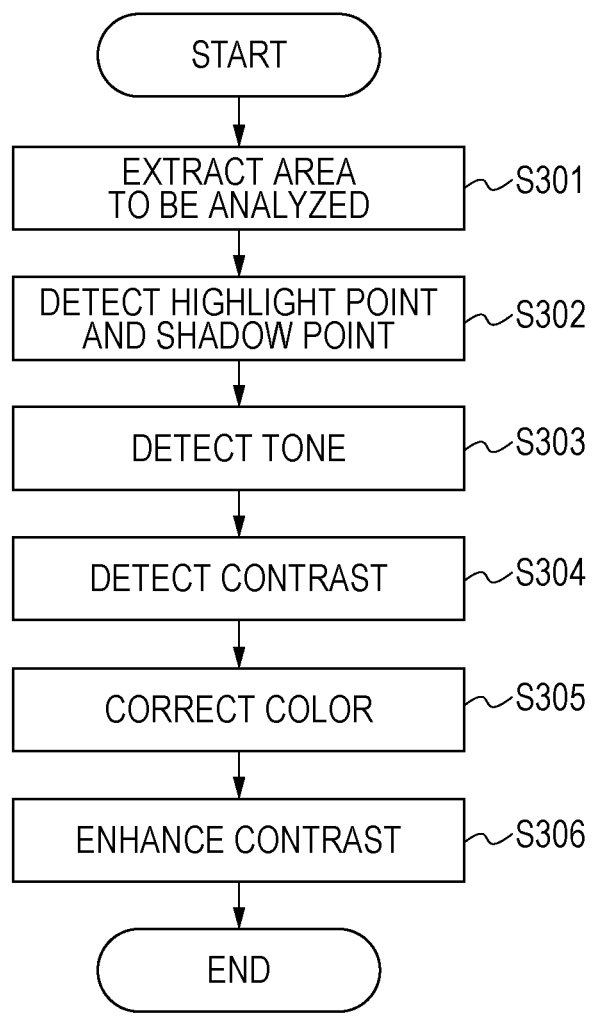

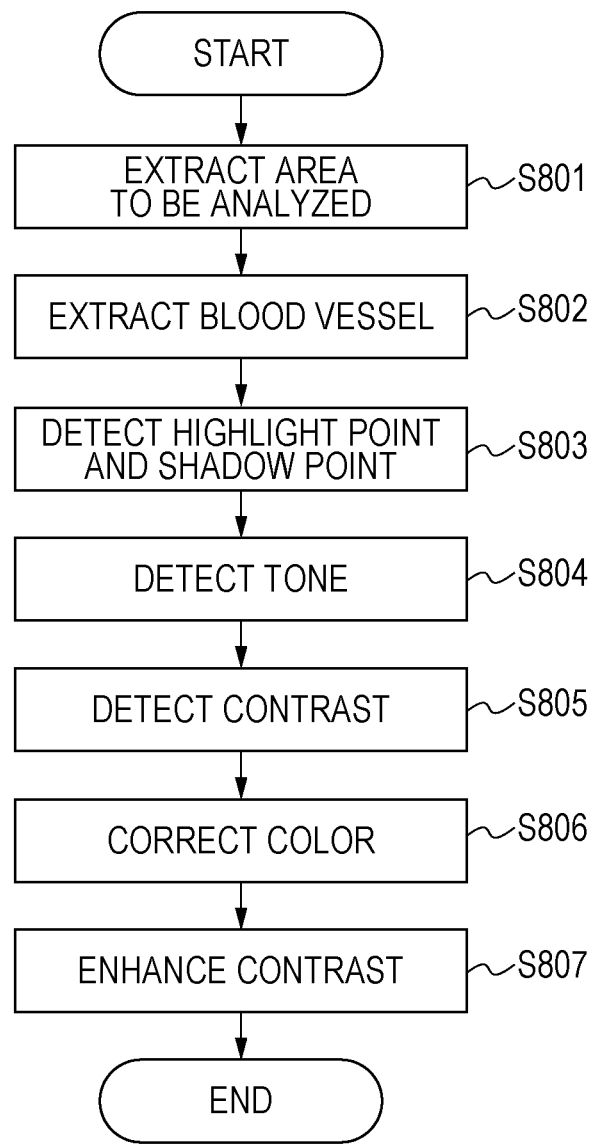

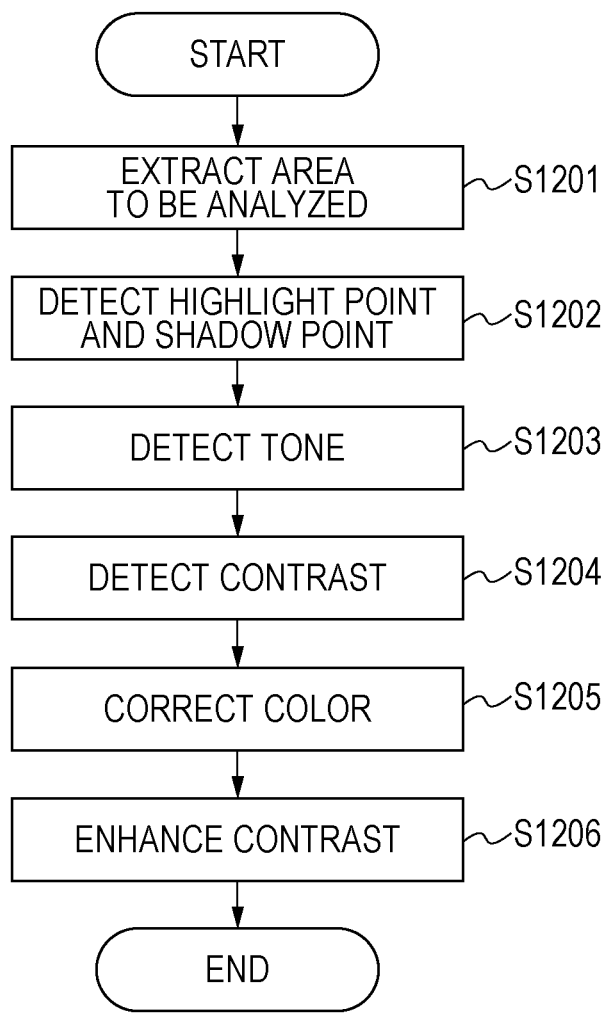

OPHTHALMOLOGIC APPARATUS, IMAGE PROCESSING METHOD, AND MEDIUM

BACKGROUND

Field

The disclosed technique generally relates to ophthalmologic apparatuses, image processing methods, and medium.

Description of the Related Art

Cataract, which causes clouding of the crystalline lens of an eye, and disorders that cause clouding of the cornea are known. Japanese Patent Laid-Open No. 2003-310556 discloses, as a method for acquiring an image of an eye of which the crystalline lens has clouded by using a slit-lamp microscope, a method in which an image is acquired with the quantity of imaging light and the gain of the blue component being reduced as the degree of the clouding of the crystalline lens rises. This method reduces an influence of reflection of the blue component on the image caused by the clouded portion.

SUMMARY

However, primarily the blue component, which is a short wavelength component, is scattered by the clouded portion, and thus the blue component contained in an image of an eye with clouding may be more reduced than the blue component contained in an image of an eye without clouding. In other words, if the quantity of the imaging light and the gain of the blue component are reduced when the clouding is present as in the existing technique, the amount of the blue component contained in the image may be further reduced.

The technique disclosed herein has been conceived of in the light of such a situation, and one of the aspects is directed to acquiring a good image of an eye with clouding.

It is to be noted that the disclosed technique is not limited to the aforementioned aspect, and another aspect of the technique can provide effects that are derived from each of the configurations described hereinafter in the exemplary embodiments and that cannot be obtained through the conventional techniques.

A disclosed ophthalmologic apparatus includes an image acquisition unit configured to acquire a fundus image of an eye to be examined on the basis of returning light from a fundus, the returning light being obtained by irradiating the fundus of the eye with light; and a correction unit configured to correct the fundus image in accordance with a degree of clouding of a clouded portion of the eye such that, among color components contained in the fundus image, a ratio of a color component, in the fundus image, that is scattered by a clouded portion of the eye at a higher rate increases against a ratio of another color component.

Further features of the present disclosure will become apparent from the following description of exemplary embodiments with reference to the attached drawings.

BRIEF DESCRIPTION OF THE DRAWINGS

FIG. 3 is a flowchart illustrating an example of image processing procedures.

FIG. 9 is a flowchart illustrating an example of image processing procedures.

FIG. 12 is a flowchart illustrating an example of image processing procedures.

DESCRIPTION OF THE EMBODIMENTS

Hereinafter, an ophthalmologic apparatus according to the present exemplary embodiment will be described with reference to the drawings. It is to be noted that configurations shown in the exemplary embodiments described hereinafter are merely illustrative, and the present invention is not limited to the configurations disclosed in the present specification and the drawings.

First Exemplary Embodiment

Configuration of Imaging Apparatus

An example of the configuration of a fundus imaging apparatus according to the present exemplary embodiment will be described with reference to FIGS. 1, 2A, and 2B. The fundus imaging apparatus corresponds to an example of an ophthalmologic apparatus.

Figure 1:
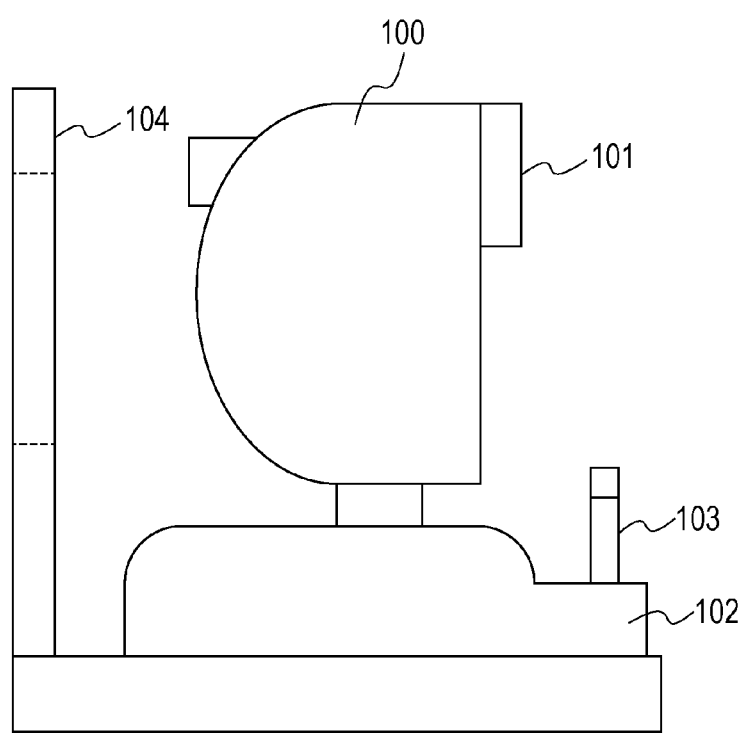
FIG. 1 illustrates an example of a configuration of a fundus imaging apparatus.
Figure 2A:
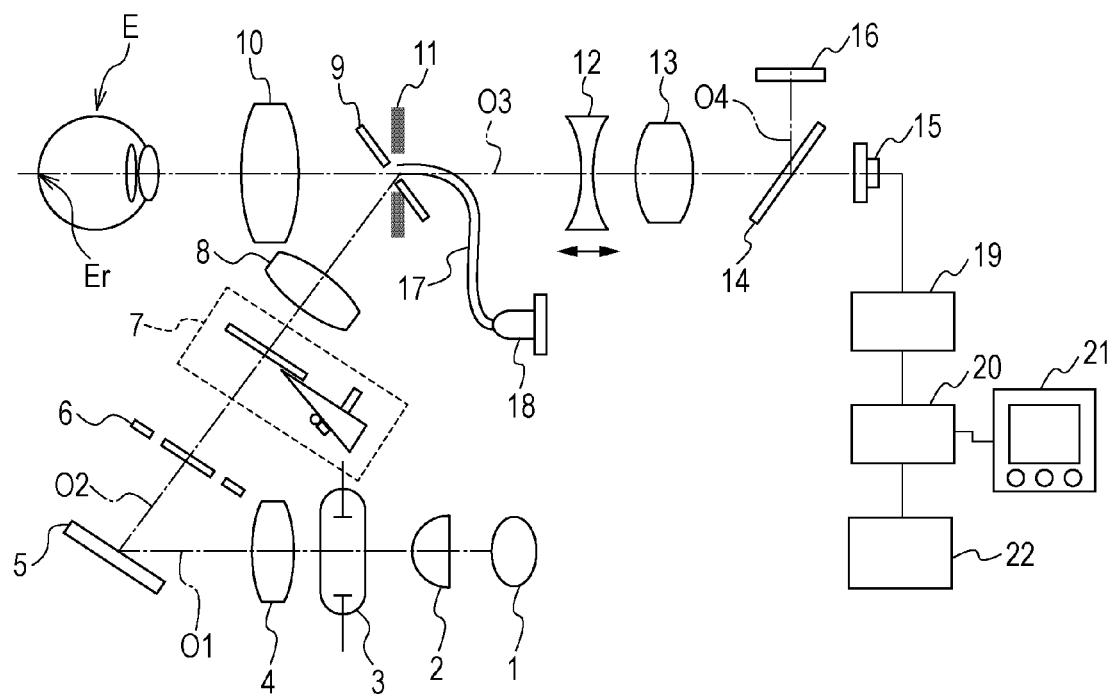
FIGS. 2A and 2B illustrate an example of a configuration of a measurement unit and a camera unit of a fundus camera.
Figure 2B:
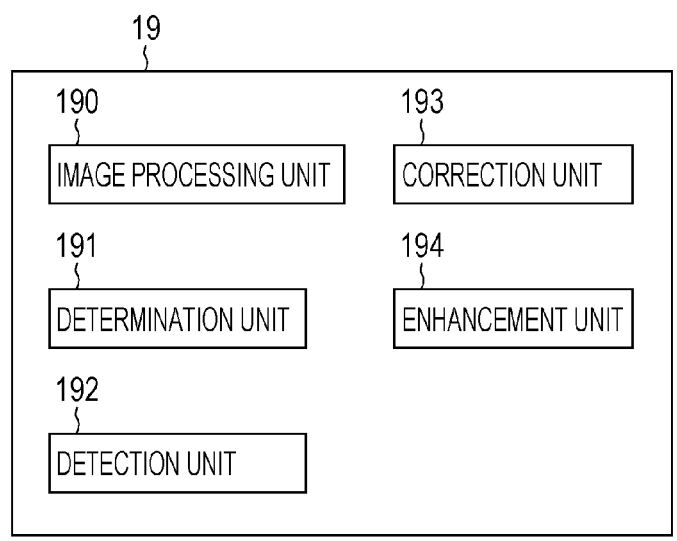

FIG. 1 is a side view illustrating an example of the configuration of the fundus imaging apparatus, and the fundus imaging apparatus includes a measurement unit 100, a camera unit 101 that includes an image sensor, a main body unit 102, a joystick 103, and a face receiver 104. Alternatively, the image sensor may be included in the measurement unit 100. Although a fundus camera is described as an example of the fundus imaging apparatus in the present exemplary embodiment, the present invention is not limited thereto, and the fundus imaging apparatus may be an apparatus other than a fundus camera, such as a scanning laser ophthalmoscope (SLO) that employs a plurality of light sources having different dominant wavelengths.

The measurement unit 100 includes an optical system for irradiating an eye to be examined with light and another optical system for guiding returning light from the eye to the image sensor. In addition, the measurement unit 100 is configured to be capable of moving three-dimensionally relative to the main body unit 102 in accordance with the operation of the joystick 103 by the examiner. Furthermore, the measurement unit 100 is configured to be capable of moving three-dimensionally relative to the main body unit 102 with a motor controlled by a processor when automatic alignment is carried out.

The camera unit 101 includes the image sensor. For example, the camera unit 101 is implemented by a main body unit of a single-lens reflex camera. The camera unit 101 may include a display unit that can display a captured image and an operation unit, such as a touch panel. The camera unit 101 may be attached to the exterior of the measurement unit 100 or may be provided in the measurement unit 100.

The main body unit 102 includes, for example, a motor for actuating the measurement unit 100 and a mechanism for transmitting the operation of the joystick 103 by the examiner to the measurement unit 100 in the form of motive power.

The joystick 103 is used to actuate the measurement unit 100. Although the joystick 103 is used to actuate the measurement unit 100 in the present exemplary embodiment, the present exemplary embodiment is not limited thereto. For example, the configuration may be such that a touch panel is used to receive the operation of the examiner and the measurement unit 100 can be actuated in accordance with the operation.

The face receiver 104 is a member for fixing the face of a subject. The face receiver 104 includes a chin receiver and a forehead pad. The chin and the forehead of the subject are fixed by the face receiver 104, and thus the eye to be examined is fixed.

Next, the detailed configuration of the fundus imaging apparatus will be described. FIGS. 2A and 2B illustrate an example of the configuration of the measurement unit 100 and the camera unit 101.

An illumination optical system is provided on optical axes O1 and O2. An observation light source 1 that includes a light-emitting diode (LED) light source configured to emit near-infrared light, a condenser lens 2, an imaging light source 3 such as an electronic flash, a lens 4, and a mirror 5 are disposed on the optical axis O1. The observation light source 1 may be constituted by a light source other than the LED light source. The imaging light source 3 is implemented, for example, by an LED light source or a xenon tube and emits, for example, visible light.

Furthermore, a ring diaphragm 6 having an annular opening formed therein, a focus target projection unit 7, a relay lens 8, and a ring mirror 9 having a center opening formed therein are successively arrayed on the optical axis O2 that extends in the direction in which the light emitted by the observation light source 1 is reflected by the mirror 5.

In addition, an objective lens 10 is disposed so as to face an eye E to be examined on an optical axis O3 that extends in the direction in which the light emitted by the observation light source 1 is reflected by the ring mirror 9. Furthermore, an imaging diaphragm 11 is provided in the opening in the ring mirror 9; and a focusing lens 12, an imaging lens 13, a mirror 14, and an image sensor 15 are successively arrayed behind the imaging diaphragm 11 (i.e., in the direction opposite to where the eye E is located).

A fixation target 16 is disposed on an optical axis O4 that extends in the direction in which returning light from the eye E is reflected by the mirror 14. The fixation target 16 includes a liquid-crystal display panel and a backlight for projecting a fixation target onto a fundus Er of the eye E at a desired position thereon, and is disposed so as to be optically conjugate to the image sensor 15.

In addition, an exit end of a light guide 17 for guiding a target light beam is disposed at a position laterally offset from the optical axis O3 in the vicinity of the opening in the ring mirror 9. An entrance end of the light guide 17 is connected to an LED light source 18 for lighting an alignment target, and the light emitted from the exit end of the light guide 17 is projected onto the eye E as an alignment target.

The image sensor 15 receives the returning light from the eye E and is implemented, for example, by a charge-coupled device (CCD). The image sensor 15 is not limited to a CCD and may instead be implemented, for example, by a complementary metal-oxide semiconductor (CMOS). The image sensor 15 is sensitive, for example, to infrared light and visible light. Alternatively, an image sensor that is sensitive to infrared light and another image sensor that is sensitive to visible light may be separately provided. The image sensor 15 is connected to an image processing unit 19.

The image processing unit 19 generates an image of the eye E on the basis of an output of the image sensor 15. Specifically, the image processing unit 19 acquires a fundus image on the basis of an output of the image sensor 15 that has received the returning light from the fundus Er. In other words, the image processing unit 19 corresponds to an example of an image acquisition unit configured to acquire a fundus image of an eye to be examined on the basis of returning light from the fundus of the eye that is obtained by irradiating the fundus with light.

In addition, the image processing unit 19 subjects the image of the eye E to predetermined image processing. The image processing unit 19 may be included in the camera unit 101 or in the measurement unit 100. Alternatively, the image processing unit 19 may be provided in an apparatus, such as a PC, that is separate from the fundus imaging apparatus.

The image processing unit 19 is implemented, for example, by a processing unit, such as a central processing unit (CPU), an application specific integrated circuit (ASIC), or a field programmable gate array (FPGA). The function of the image processing unit 19 will be described in further detail. As the processing unit such as a CPU executes a program stored in a read-only memory (ROM) (not illustrated), the image processing unit 19 functions as an image generation unit 190, a determination unit 191, a detection unit 192, a correction unit 193, and an enhancement unit 194, as illustrated in FIG. 2B.

The processing unit such as the CPU and a storage unit such as the ROM may each be provided singly or in plurality. In other words, at least one or more processing units (CPU) and at least one or more storage units (ROM, etc.) are connected; and when the at least one or more processing units execute a program stored in the at least one or more storage units, the processing unit such as the CPU functions as each of the aforementioned units.

The image generation unit 190 generates an image of the eye E on the basis of an output of the image sensor 15. More specifically, the image generation unit 190 generates a fundus image of the eye E. The image generation unit 190 generates, for example, a black and white image on the basis of the returning light, from the eye E, of the light emitted by the observation light source 1 and generates a color image on the basis of the returning light, from the eye E, of the light emitted by the imaging light source 3.

The determination unit 191 determines a region for extracting color components in the image generated by the image generation unit 190. More specifically, the determination unit 191 sets a predetermined region in the fundus image and determines a region corresponding to an optic disc within the predetermined region. The determination unit 191 then determines a region that does not contain the optic disc as a region for extracting the color components (i.e., the region to be processed by the detection unit 192). The determination unit 191, for example, divides the set region into a plurality of small regions and obtains a mean value of luminance in each of the small regions. The determination unit 191 then identifies a small region with high luminance within the set region as a region corresponding to the optic disc. Alternatively, the determination unit 191 may identify a small region with a mean luminance value that is equal to or greater than a predetermined threshold as a region corresponding to the optic disc. Here, an approximate size of the optic disc may be stored in a storage unit (not illustrated), and small regions that each have high luminance within the set region and that are of a size corresponding to the size of the optic disc may be identified as a region corresponding to the optic disc. The aforementioned size may be set to a size greater than a typical size of an optic disc with the robustness taken into consideration.

The determination unit 191 may identify, as a region corresponding to the optic disc, small regions of a size corresponding the stored size of the optic disc with a small region having the highest luminance within the set region situated at the center. The storage unit (not illustrated) is constituted by a random-access memory (RAM), a ROM, a hard disk drive (HDD), a solid state drive (SSD), or the like.

Alternatively, the determination unit 191 may detect the optic disc on the basis of the luminance of a fundus image prior to setting any region in the fundus image and may set a region in the fundus image so as to exclude the optic disc.

The determination unit 191 may then exclude, from a processing target of the detection unit 192, a portion of the set region in which the mean luminance of each small region is lower than a predetermined threshold. With such a configuration, a portion of the fundus image having extremely high luminance and a portion having extremely low luminance can be excluded from the processing target, and the reliability of image processing can thus be improved. An example of a portion having mean luminance that is lower than a predetermined value may be a macula lutea in the fundus.

Although the mean luminance of the small region is used in the above examples, any one of the maximum value, the minimum value, and the median value of the luminance in the small region may instead be used.

The detection unit 192 detects a highlight point (bright portion) and a shadow point (dark portion) in the region determined by the determination unit 191. In other words, the detection unit 192 corresponds to an example of a detection unit configured to detect a highlight point and a shadow point on the basis of the luminance distribution of a fundus image.

More specifically, the detection unit 192 detects a highlight point and a shadow point on the basis of the luminance distribution of a region excluding the optic disc.

The detection unit 192 detects, for example, a luminance value that is at the fifth percentile from the high luminance side in the region determined by the determination unit 191, as the highlight point. In addition, the detection unit 192 detects, for example, a luminance value that is at the eighth percentile from the low luminance side in the region determined by the determination unit 191, as the shadow point. Here, the luminance value to be detected as the highlight point may be a luminance value other than the luminance value at the fifth percentile from the high luminance side. In addition, the luminance value to serve as the highlight point may span a range of values, such as the luminance values that fall in the range from the first to the fifth percentile from the high luminance side. Meanwhile, the luminance value to be detected as the shadow point may be a luminance value other than the luminance value at the eighth percentile from the low luminance side. In addition, the luminance value to serve as the shadow point may span a range of values, such as the luminance values that fall in the range from the first to the eighth percentile from the low luminance side.

The detection unit 192 further obtains the mean of color information of the highlight point and of the shadow point. For example, the detection unit 192 obtains the mean of color information of the highlight point by averaging the respective values of R, G, and B at the highlight point. Alternatively, the mean may be obtained by using a different piece of information, such as the information on Y, Cb, and Cr. As another alternative, instead of using the mean value, the maximum value, the minimum value, or the median value may be used.

Furthermore, the detection unit 192 maps the mean value of the color information of each of the highlight point and the shadow point onto a color space. Specifically, the detection unit 192 maps the mean value of the color information of each of the highlight point and the shadow point in a coordinate system in which the vertical axis represents the luminance Y and the horizontal axis represents Cb. The detection unit 192 then acquires, as a tone of the image, an angle of a straight line connecting the mapped highlight point and shadow point relative to the vertical axis and stores this angle into the storage unit. The angle to be acquired is not limited to the angle relative to the vertical axis and may be an angle of the straight line connecting the highlight point and the shadow point relative to the horizontal axis. The coordinate system in which the highlight point and the shadow point are mapped is not limited to the Y-Cb coordinate system and may be a different coordinate system, such as the Y-Cr coordinate system.

In addition, the detection unit 192 detects, as a contrast value, a luminance difference between the mapped highlight point and shadow point. The detected contrast value is stored into the storage unit (not illustrated).

Aside from the highlight point and the shadow point, the detection unit 192 may extract, for example, a point at a luminance value intermediate between the highlight point and the shadow point from the fundus image, and may carry out the above-described processing by using an approximation straight line of these three points. In other words, the points that the detection unit 192 detects are not limited to the two points: the highlight point and the shadow point. In addition, the detection unit 192 may carry out the above-described processing on the basis of a straight line that passes through the shadow point or the highlight point and the point at the luminance value intermediate between the highlight point and the shadow point.

The correction unit 193 carries out a color correction (rotational transformation) of the image generated by the image generation unit 190 such that the angle detected by the detection unit 192 approaches an angle formed by a straight line connecting a highlight point and a shadow point in the image of an eye without clouding and the vertical axis representing the luminance Y. For example, the correction unit 193 corrects the image by rotating the straight line connecting the highlight point and the shadow point about the intersection of the vertical axis and the horizontal axis (i.e., the origin) or about the shadow point. The correction method will be described later in detail.

The goal of the color correction is ideally the angle formed by the straight line connecting the highlight point and the shadow point in the image of the eye without clouding and the vertical axis representing the luminance Y, but is not limited to the angle in an image of an eye that is completely free of clouding. In addition, the mean value of such angles in a plurality of images may be used as the goal of the color correction.

Furthermore, the correction unit 193 corrects the contrast value detected by the detection unit 192 (i.e., contrast correction) with the luminance difference between the highlight point and the shadow point in the image of the eye without clouding serving as the goal. The goal of the contrast correction is ideally the luminance difference between the highlight point and the shadow point in the image of the eye without clouding, but is not limited to the luminance difference in the image of an eye that is completely free of clouding.

The correction unit 193 may carry out both the rotational transformation and the correction of the contrast value or may carry out only one of the rotational transformation and the correction of the contrast value.

The enhancement unit 194 carries out contrast enhancing processing on the image of the eye E. For example, the enhancement unit 194 carries out the contrast enhancing processing in accordance with the luminance difference (contrast value) between the highlight point and the shadow point detected by the detection unit 192. For example, the enhancement unit 194 reduces the contrast enhancement amount as the contrast value detected by the detection unit 192 is higher. This processing makes it possible to prevent excessive contrast enhancement.

A control unit 20 is implemented by a processing unit, such as a CPU, and carries out various types of controls in accordance with programs. For example, the control unit 20 controls light emission of the observation light source 1 and the imaging light source 3. In addition, the control unit 20 causes the image that has been subjected to the image processing by the image processing unit 19 to be displayed on a monitor 21. Furthermore, the control unit 20 stores the image generated by the image generation unit 190 and the image that has been subjected to the image processing by the image processing unit 19 into a storage unit (not illustrated). In addition, the control unit 20 can read out an image stored in the storage unit and cause the image processing unit 19 to process the image. More specifically, when an instruction for the image processing is input to the control unit 20 by the examiner through an operation unit 22, the control unit 20 reads out an image stored in the storage unit and causes the image processing unit 19 to carry out the image processing.

In addition, the control unit 20 may include a unit for detecting the presence of clouding from the acquired image of an anterior eye portion of the eye E, and control the image processing unit 19 to automatically carry out the above-described image processing if the clouding is detected. The technique for obtaining the clouding from the image of the anterior eye portion can be implemented by a variety of known techniques.

The control unit 20 may be included in the camera unit 101 or in the measurement unit 100. Alternatively, the control unit 20 may be provided in an apparatus, such as a PC, that is separate from the fundus imaging apparatus. The control unit 20 is connected to the image processing unit 19, the monitor 21, and the operation unit 22.

The monitor 21 displays the image of the eye E (e.g., fundus image) generated by the image generation unit 190. More specifically, the monitor 21 displays a black and white image that is based on the returning light, from the eye E, of the light emitted by the observation light source 1 and a color image that is based on the returning light, from the eye E, of the light emitted by the imaging light source 3. The monitor 21 may be included in the camera unit 101 or may be provided separately from the camera unit 101. In a case in which the monitor 21 is provided in the camera unit 101, the monitor 21 corresponds, for example, to a rear liquid-crystal display of a camera constituting the camera unit 101.

The operation unit 22 includes at least one of a mouse, a keyboard, a touch panel, and an imaging switch. The examiner can issue an image processing instruction or the like to the control unit 20 through the operation unit 22. The operation unit 22 may include the joystick 103. In addition, the operation unit 22 may be provided in an apparatus, such as a PC, that is separate from the fundus imaging apparatus. In a case in which the monitor 21 has the function of a touch panel, the operation unit 22 is provided in the monitor 21.

When a fundus image of the eye E is to be captured by the fundus imaging apparatus configured as described above, the control unit 20 first turns on the observation light source 1. The light beam emitted by the observation light source 1 is condensed by the condenser lens 2 and travels through the lens 4, the mirror 5, and the ring diaphragm 6 so as to be shaped into a ring light beam. Thereafter, the ring light beam travels through the relay lens 8 and is deflected by the ring mirror 9 in the direction of the optical axis O3. The ring light beam then travels through the objective lens 10 and illuminates the fundus Er of the eye E.

The light beam that has reached the fundus Er is reflected and scattered by the fundus Er and is emitted from the eye E as a fundus reflection image. This light beam passes through the objective lens 10, the imaging diaphragm 11, the focusing lens 12, and the imaging lens 13 and is then imaged on the image sensor 15. The control unit 20 acquires an output of the image sensor 15 and displays, on the monitor 21, the fundus image captured by the observation image sensor 15.

The examiner fine-tunes the positioning of the eye E and the optical unit and adjusts the focus while observing the fundus image displayed on the monitor 21. The examiner then captures the image by pressing the imaging switch included in the operation unit 22. Upon the imaging switch being pressed, the control unit 20 causes the imaging light source 3 to emit light, and the eye E is thus illuminated by visible light for imaging. The returning light of this light from the fundus Er is imaged on the image sensor 15. Then, as in the observation image, the fundus image is displayed on the monitor 21 by the control unit 20. The image captured by using the observation light source 1 is a black and white image, and the image captured by using the imaging light source 3 is a color image.

The captured image is stored in the storage unit inside the fundus imaging apparatus (not illustrated) connected to the control unit 20. The image stored in the storage unit inside the fundus imaging apparatus is read out as appropriate and displayed on the monitor 21, as the operation unit 22 is operated. In addition, an external storage unit and an external computer can be connected to the control unit 20, and the control unit 20 can transfer the captured image to such external devices.

Image Processing

Subsequently, an example of the processing procedures of the image processing unit 19 will be described with reference to FIGS. 3 to 8.

An example of the flow of the image processing according to the present exemplary embodiment is illustrated in FIG. 3. In the present exemplary embodiment, described is a case in which the image processing unit 19 carries out the image processing on a captured image (e.g., a color fundus image) that the control unit 20 has read out from the storage unit on the basis of an instruction from the operation unit 22. The control unit 20 may read out the image from an internal storage unit or an external storage unit of the fundus imaging apparatus.

Figure 4:
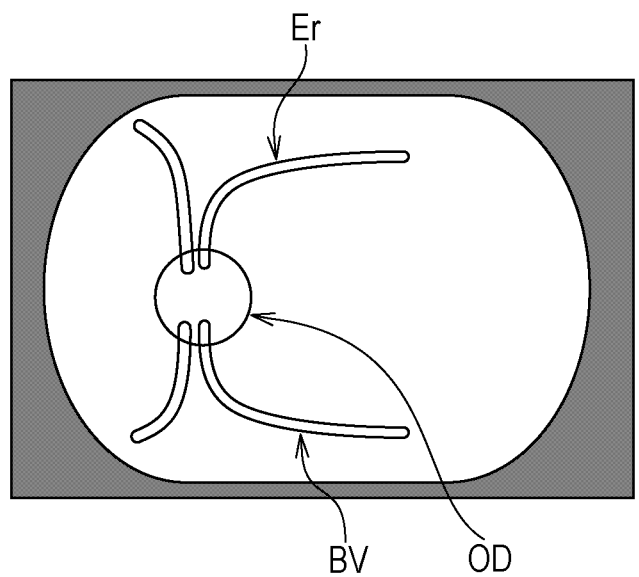
FIG. 4 illustrates an example of a fundus image.

In step S301, the determination unit 191 determines an area to be analyzed by the detection unit 192. FIG. 4 illustrates an example of a schematic diagram of a captured image of the fundus Er captured in the composition called the posterior pole center. FIG. 4 illustrates an optic disc OD and a blood vessel BV. The optic disc OD is an organ that appears extremely bright relative to the remaining retina portion.

In a typical image correction of an image other than a fundus image, a bright area is extracted as a highlight point, and a dark area is extracted as a shadow point. Then, image processing in which the image is converted so that the bright area becomes white and the dark area becomes black is carried out. If such image processing is carried out on a fundus image, the optic disc is extracted as the highlight point, and the optic disc is converted to a white area as a result of the processing. However, if the optic disc appears too white, a disease such as glaucoma can be suspected. Therefore, making the optic disc appear too white is inappropriate in color conversion processing of the fundus image. In addition, it is known that the brightness and the tone of the optic disc vary depending on the diseases.

Accordingly, in the present exemplary embodiment, an area in which the highlight point and the shadow point are to be extracted is set to a retina portion excluding the optic disc, and thus the above-described problem is solved. Thus, the optic disc does not appear too white, and the analysis result is less likely to be affected by the disease of the optic disc.

Figure 5:
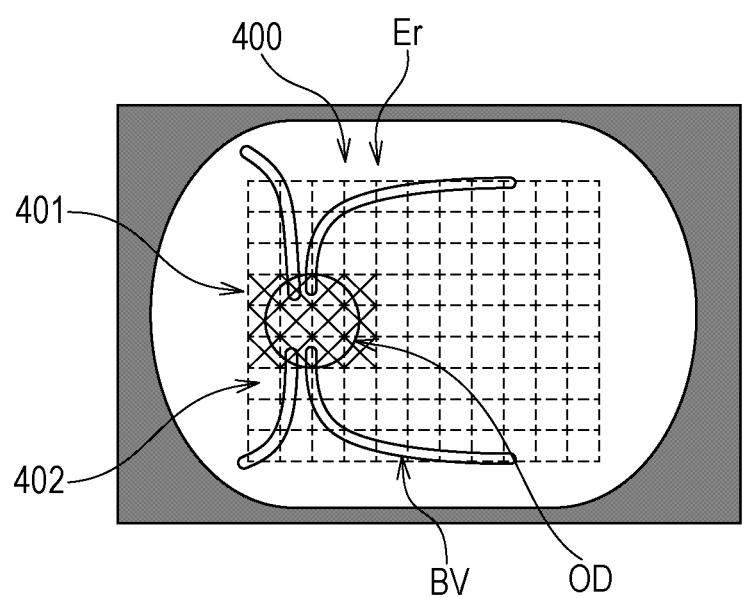
FIG. 5 illustrates an example of an analysis area set in a fundus image.

Specifically, as illustrated in FIG. 5, the determination unit 191 sets an initial analysis area 400 at a center portion of the fundus image and divides the initial analysis area 400 into sub-areas (small regions) in a mesh pattern. It is to be noted that the size and the position of the initial analysis area 400 may be made variable.

The determination unit 191 then obtains a mean luminance value in each of the sub-areas divided in the mesh pattern. Here, with the use of the information on the approximate size of the optic disc OD stored in advance in the storage unit, the determination unit 191 detects, from the entire initial analysis area 400, a set of sub-areas that span an area corresponding to the size of the optic disc and that each have brightness equal to or greater than a threshold, and excludes the detected sub-areas from the analysis area. Thus, the optic disc OD is excluded from the analysis area. FIG. 5 illustrates the excluded sub-areas 401 and the remaining sub-areas 402 that are not excluded. The sub-areas 401 are each marked by x.

Through the processing described above, the determination unit 191 determines a region in the fundus image in which the highlight point and the shadow point are to be extracted.

Figure 6:
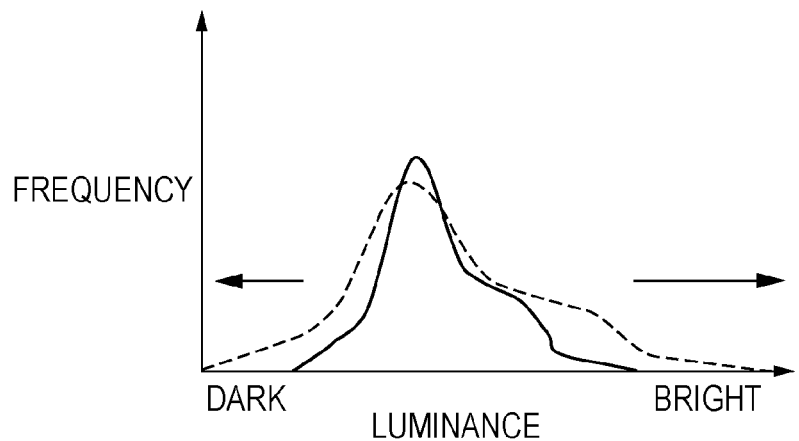
FIG. 6 illustrates an example of histograms of a fundus image.

In step S302, the detection unit 192 generates a histogram (luminance distribution) of the region determined by the determination unit 191 and detects the highlight point and the shadow point. FIG. 6 illustrates an example of the histogram of the fundus image.

In the present exemplary embodiment, the highlight point corresponds to the luminance value at the fifth percentile from the bright side, and the mean of the color information of the pixels having the luminance value of the highlight point is retained as the color of the highlight point. Meanwhile, on the dark side, the shadow point corresponds to the luminance value at the eighth percentile from the dark side, and the mean of the color information of the pixels having the luminance value of the shadow point is retained as the color of the shadow point.

Here, the reason why the shadow point is set at the eighth percentile from the dark side will be described. Sites that appear dark on the fundus include a blood vessel, or in particular, a vein. The color of the vein reflects the color of blood, and thus it has been found experimentally that there are little individual differences in tone. Therefore, in the present exemplary embodiment, the luminance value of the shadow point is set such that part of the blood vessel, which is a site with little individual differences, can be included in the shadow point. Of course, this numerical value is influenced by the size and the position of the analysis area described above, and may thus be changed as appropriate in accordance with the size and the position of the analysis area. The numerical value may be set so that part of the blood vessel is included. In addition, although the highlight point is set at the luminance value at the fifth percentile from the bright side so as to exclude a high luminance portion that is produced by noise and the like, a luminance value at a different value may instead be used.

In other words, the luminance value to be detected as the highlight point and the luminance value to be detected as the shadow point are not limited to the above-described values.

Figure 7:
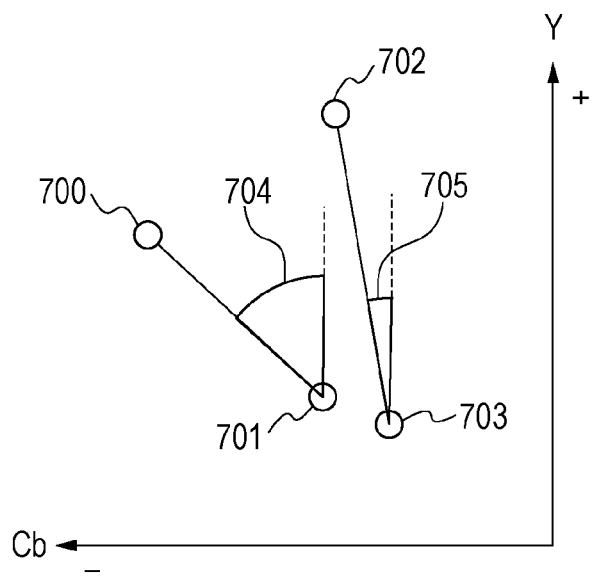
FIG. 7 illustrates an example of a highlight point and a shadow point in a color space.

In step S303, the detection unit 192 detects the tone of the fundus image with the use of the highlight point and the shadow point. An example of the processing for detecting the tone will be described with reference to FIG. 7. FIG. 7 illustrates the highlight point and the shadow point of the fundus image being plotted in the YCbCr color space and illustrates a projection on the Y-Cb space. The axis representing Cb takes a smaller value (a greater negative value) toward the left side of the paper plane, and the axis representing Y takes a greater value toward the upper side of the paper plane. The axis representing Cr extends in the direction orthogonal to the paper plane and is thus omitted in the drawing. Here, the coordinate axes representing Cb and Y correspond to an example of predetermined coordinate axes for defining the color space.

The color space used in the present exemplary embodiment is the YCbCr space. This color space is selected because it takes less work to convert the RGB color space, in which the captured image is retained, into the YCbCr color space. However, similar processing may be carried out in any color space, including the RGB color space, the XYZ color space, and L*a*b* color space.

FIG. 7 illustrates a highlight point 700 of a typical eye with cataract and a shadow point 701 of the same eye with cataract. Although the image processing on the fundus image of an eye with cataract is illustrated as an example in the present exemplary embodiment, the image processing of the disclosure can also be applied to a fundus image of an eye with corneal clouding.

FIG. 7 further illustrates a highlight point 702 of an eye without cataract and a shadow point 703 of the same eye without cataract. It can be seen that the shadow points of the eye with cataract and of the eye without cataract fall at substantially the same position but the highlight points are largely offset from each other in the Cb-direction. The Y-axis direction and the straight line connecting the highlight point and the shadow point of the eye with cataract form an angle 704, and the Y-axis direction and the straight line connecting the highlight point and the shadow point of the eye without cataract form an angle 705. FIG. 7 reveals that the two angles 704 and 705 differ from each other. It can be speculated that this difference is produced because the color tone of the fundus image is shifted in the yellow direction as a result of a short-wavelength component (blue component) of the incident light for imaging having been scattered due to the clouding caused by cataract. Therefore, capturing the image of an eye with cataract results in an image with a yellow overlay, as compared to the image of an eye without cataract, and the resulting image makes it harder to visually recognize features such as the blood vessel in the fundus.

It is to be noted that the eye without cataract is a concept that encompasses an eye that is completely free of clouding and an eye with clouding that is at a level less than a predetermined threshold. In other words, the angle 705 corresponds to an example of a predetermined angle formed by the straight line connecting the highlight point and the shadow point obtained from the luminance distribution of the fundus image of an eye with clouding that is at a level less than a threshold and a predetermined coordinate axis defining the color space.

As illustrated in FIG. 7, the detection unit 192 maps the highlight point 700 and the shadow point 701 in the YCbCr color space with the use of the color of the highlight point and the color of the shadow point obtained in step S302. The detection unit 192 then detects, as the tone of the fundus image, the angle 704 formed by the straight line connecting the highlight point 700 and the shadow point 701 and the vertical axis. Then, the detection unit 192 stores the detected angle 704 into the storage unit. The angle 705 associated with the eye without cataract, for example, is stored in advance in the storage unit by carrying out in advance the processing similar to the processing carried out on the image of the eye with cataract. Instead of detecting the angle 705 by the fundus imaging apparatus; the angle 705 may be detected by another apparatus; or if any known value is present, that value may be stored in the storage unit.

In step S304, the detection unit 192 detects the contrast in the fundus image. Specifically, the detection unit 192 detects, as the contrast value, the difference between the luminance of the highlight point 700 and the luminance of the shadow point 701 (i.e., luminance difference). The detection unit 192 stores the detected contrast value into the storage unit. The detection unit 192 also detects in advance the difference between the luminance of the highlight point 702 and the luminance of the shadow point 703 of the eye without cataract and stores the detected difference in the storage unit. Instead of detecting the contrast in the image of the eye without cataract by the fundus imaging apparatus, the contrast may be detected by another apparatus; or if any known value is present, that value may be stored in the storage unit.

Although the captured image is used as-is in the processes in steps S302 to S304 of the present exemplary embodiment, a reduced thumbnail image may instead be used in order to increase the processing speed, or whether to use the captured image or the thumbnail image may be determined on the basis of the image size, set by the examiner, serving as a threshold. In addition, the image size of the thumbnail image may be changed as appropriate. Step S303 and step S304 may be carried out in a reverse order or may be carried out in parallel.

In step S305, the correction unit 193 carries out the color correction of the fundus image. This color correction includes the rotational transformation that brings the angle 704 detected in step S303 closer to the angle 705. Furthermore, the color correction carried out in step S305 includes a transformation of elongating the luminance difference between the highlight point 700 and the shadow point 701 obtained after the rotational transformation so as to be brought closer to the luminance difference between the highlight point 702 and the shadow point 703.

A specific example of the rotational transformation will be described. The correction unit 193 rotates the straight line connecting the highlight point 700 and the shadow point 701 about the intersection of the vertical axis and the horizontal axis (i.e., the origin) or about the shadow point 701 so as to bring the angle 704 closer to the angle 705. Ideally, the correction unit 193 carries out the color correction of the fundus image such that the angle 704 becomes equal to the angle 705. The angle 704 may not be made exactly equal to the angle 705, and the correction unit 193 may carry out the color correction of the fundus image such that the difference between the angle 704 and the angle 705 falls within a predetermined threshold. The difference between the angle 704 and the angle 705 represents a difference corresponding to the degree of clouding. Here, the color correction of bringing the angle 704 closer to the angle 705 can be regarded as a correction of increasing the value of Cb. In other words, the rotational transformation is a correction of making the ratio of the blue component, in the image, that is primarily scattered by the clouding increase against the ratios of the other color components. In other words, the correction unit 193 corresponds to an example of a correction unit configured to correct a fundus image in accordance with the degree of clouding of an eye to be examined such that, among the color components contained in the fundus image, the ratio of a color component, in the fundus image, that is scattered by a clouded portion of the eye at a higher rate is made to increase against the ratios of the other color components. Specifically, the ratio of the blue component, in the image, that is a color component scattered at a higher rate by the clouded portion is made to increase against the ratios of the red component and of the green component.

Here, the angle 704 corresponds to an example of an angle formed by the straight line connecting a highlight point and a shadow point in a color space and a predetermined coordinate axis defining the color space. In other words, the color correction of bringing the angle 704 closer to the angle 705 in step S305 is an example of a correction of making, among the color components contained in a fundus image, the ratio of a color component, in the fundus image, that is scattered by a clouded portion of the eye at a higher rate increase against the ratios of the other color components, so that the angle formed by the straight line connecting the highlight point and the shadow point in the color space and the predetermined coordinate axis defining the color space approaches a predetermined angle.

As it is clear from FIG. 7, the correction amount in this color correction differs in accordance with the luminance. For example, an image closer to the highlight point 700 is corrected more than an image closer to the shadow point 701. The correction unit 193 generates information such as a table indicating a relation between the luminance and the correction amount and stores such information in the storage unit. The stored information such as the table may be used when the image processing is carried out again on a fundus image. The relation between the luminance and the correction amount may be stored not in the form of a table but in the form of a transformation expression. In addition, the correction unit 193 may generate a table or a transformation expression that maps the color information with the correction amount and store the generated table or transformation expression. For example, (Y',Cb',Cr') obtained after the rotation φ (Rφ) of (Y,Cb,Cr) in the Cr-axis direction is computed through the following transformation expression (rotational transformation). The correction unit 193 carries out this transformation on the entire pixels.

$$\begin{pmatrix} Y' \\ Cb' \\ Cr' \end{pmatrix} = \begin{pmatrix} \cos\phi & -\sin\phi & 0 \\ \sin\phi & \cos\phi & 0 \\ 0 & 0 & 1 \end{pmatrix} \begin{pmatrix} Y \\ Cb \\ Cr \end{pmatrix} \quad (1)$$

In addition, the correction intensity may be varied between the bright portion and the dark portion of the fundus image. In other words, the correction intensity may be changed in accordance with the luminance of the image. Here, the correction intensity is a coefficient by which the correction amount necessary for making the angle 704 equal to the angle 705 is multiplied. For example, the correction intensity in the luminance value from the highlight point 700 to the shadow point 701 in the image may be set to 1, and the correction intensity of a black dot with a luminance value of 0 and a white dot with a luminance value of 255 may be set to 0. In addition, the correction intensity may be changed such that the correction intensity decreases toward the white dot in pixels with the luminance in the range from the highlight point 700 to the white dot. In a similar manner, the correction intensity may be changed such that the correction intensity decreases toward the black dot in pixels with the luminance in the range from the shadow point 701 to the black dot. The table that indicates the value of the correction intensity relative to the luminance is stored in advance in the storage unit, and the correction unit 193, when carrying out the image processing, may carry out the color correction of the fundus image on the basis of the table indicating the relation between the luminance and the correction amount and the table indicating the relation between the luminance and the correction intensity.

As the color correction is carried out with the use of the relation between the luminance and the correction intensity, the correction intensity of the pixels in the bright portion and the dark portion in the fundus image is reduced as compared to the correction intensity of the pixels with mean luminance. Thus, the optic disc that is brighter than the highlight point 700 can be prevented from appearing too white, and the area that is darker than the shadow point 701 can be prevented from appearing too dark. In other words, a good fundus image suitable for making a diagnosis can be obtained.

Furthermore, the correction unit 193 may add translation by which the shadow point 701 detected so as to match the tone of the blood vessel portion is brought closer to the shadow point 703 serving as a target. For example, the correction unit 193 may detect the difference between the coordinate of the shadow point 701 and the coordinate of the shadow point 703 and may make a correction by translating, in the color space, the pixels in the fundus image including the pixels ranging from the highlight point 700 to the shadow point 701 on the basis of the detected difference. The rotational transformation and the translation may be carried out in any order.

In addition, in the present exemplary embodiment, the highlight point and the shadow point are detected in the Y-Cb space with the use of the YCbCr color space, and thus the transformation is a rotational transformation about the Cr-axis. However, similar processing may be carried out in the Y-Cr space, and the rotational transformation about the Cb-axis may be carried out.

Furthermore, the highlight point 702 and the shadow point 703 illustrated in FIG. 7 may be set as the targets of the transformation, and a transformation matrix may be set such that the detected highlight point 700 and shadow point 701 approach the targets. In this case, in order to increase the accuracy of the transformation, a point between the highlight point and the shadow point may be retained in step S302 described above to interpolate between the highlight point and the shadow point.

In addition, as described above, a different color space may be used. For example, in the L*a*b* space, the direction of b* corresponds to the direction of the yellow tone; thus, the highlight point and the shadow point may be detected in the L*-b* space, and the rotational transformation may be carried out about the a*-axis.

After the rotational transformation described above, the correction unit 193 carries out the transformation of elongating the luminance difference between the highlight point 700 and the shadow point 701 so as to be brought closer to the luminance difference between the highlight point 702 and the shadow point 703. The solid line illustrated in FIG. 6 indicates the histogram of the fundus image obtained after the rotational transformation, and the dotted line indicates the histogram of the fundus image obtained after the elongation transformation. As illustrated in FIG. 6, the processing of increasing the luminance difference between the highlight point 700 and the shadow point 701 is carried out. The elongation transformation may be carried out prior to the rotational transformation. In addition, the elongation transformation may also be carried out in a color space other than the YCbCr space.

In step S306, the enhancement unit 194 enhances the contrast in the fundus image. In the present exemplary embodiment, unsharp masking processing is applied to the image in order to enhance the contrast. Typically, the unsharp masking processing includes such parameters as the size of an unsharp mask (size of the processing mask), the enhancement amount, and the threshold at which the processing is carried out. The size of the processing mask is larger than the size of a processing mask typically used in image processing and is set to the size at which an artery and a vein in the retina are enhanced.

Figure 8:
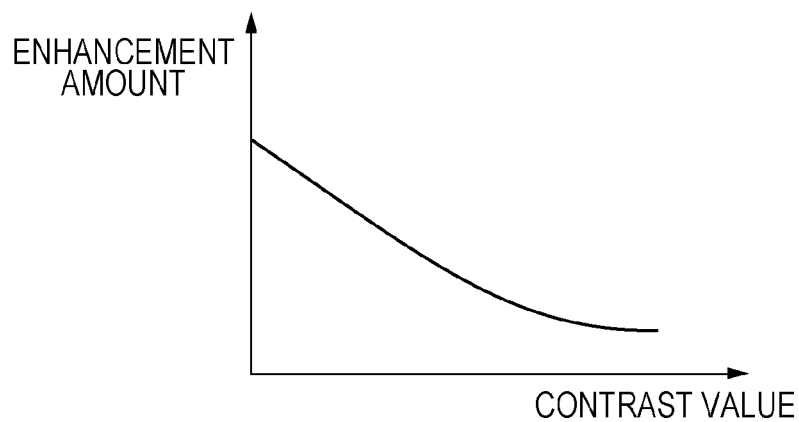
FIG. 8 illustrates an example of the characteristics of an enhancement amount relative to a contrast value.

The enhancement amount is determined on the basis of the contrast value detected and stored in step S304. It is considered that, as the contrast value is greater, the factors, such as the clouding, that hinder the visual recognizability of the image are lower. Thus, the enhancement amount is determined in accordance with the contrast value in order to prevent excessive enhancement. FIG. 8 illustrates an example of a table for determining the enhancement amount from the contrast value. In the example illustrated in FIG. 8, the enhancement amount is greater as the contrast value is smaller. This makes it possible to prevent excessive enhancement when the contrast value is large; whereas a larger enhancement amount is set when the contrast value is small, and thus a fundus image in which a blood vessel or the like is visually recognized readily can be obtained. In other words, the enhancement unit 194 corresponds to an example of a correction unit configured to enhance the contrast in a fundus image in accordance with the luminance difference (contrast value). More specifically, the enhancement unit 194, which corresponds to an example of the correction unit, reduces the enhancement degree of the contrast as the luminance difference is greater, as illustrated in FIG. 8.

Through the processing in step S306, the image correction in which the contrast is adaptively enhanced can be achieved. The image that has been subjected to the image processing described above is recorded into the storage unit by the control unit 20, and the control unit 20 displays, on the monitor 21, the fundus image that has been subjected to the image processing. The control unit 20 may display, side by side, the images before and after the image processing or may display the images such that the images before and after the image processing can be switched therebetween.

Through the image processing described thus far, a good fundus image can be obtained even if there is clouding of an eye to be examined. Specifically, the ratio of the blue component is made to increase against the ratios of the other color components, and thus a deterioration of the contrast of the blood vessel or the like can be prevented even if there is clouding of an eye to be examined.

Second Exemplary Embodiment

A second exemplary embodiment will be described. In the present exemplary embodiment, a function of detecting a blood vessel is added to the configuration of the first exemplary embodiment. The configuration of the apparatus is substantially the same as that of the first exemplary embodiment, and thus detailed descriptions thereof will be omitted.

An example of the processing procedures of the image processing unit 19 according to the second exemplary embodiment will be described with reference to FIGS. 9, 10A, and 10B. FIG. 9 is a flowchart illustrating an example of the image processing according to the present exemplary embodiment.

In the present exemplary embodiment, described is a case in which the image processing unit 19 carries out the image processing on a captured image that the control unit 20 has read out from the storage unit on the basis of an instruction from the operation unit 22. The control unit 20 may read out the image from an internal storage unit or an external storage unit of the fundus imaging apparatus.

In step S801, the determination unit 191 determines an area to be analyzed by the detection unit 192. The processing in step S801 is the same as the processing in step S301 of the first exemplary embodiment, and thus detailed descriptions thereof will be omitted.

In step 3802, the detection unit 192 extracts a blood vessel from the fundus image. A purpose of extracting a blood vessel is to match the shadow point, which is set through the histogram analysis in the first exemplary embodiment, to a blood vessel portion with higher accuracy. Another purpose is to optimize the size of a filter for the contrast enhancing processing, which will be described later.

The blood vessel is extracted, for example, by detecting an edge portion with a Gabor filter. A plurality of types of Gabor filters are set so as to provide sensitivity to blood vessels other than a thick artery and a vein that run from the optic disc. This is because the thick artery and the vein that run from the optic disc are not included in a fundus image that does not include a papilla. Filters that are thick and are of six directions at 0, 30, 60, 90, 120, and 150 degrees are used. The directions are not limited to the six directions.

Figure 10A:
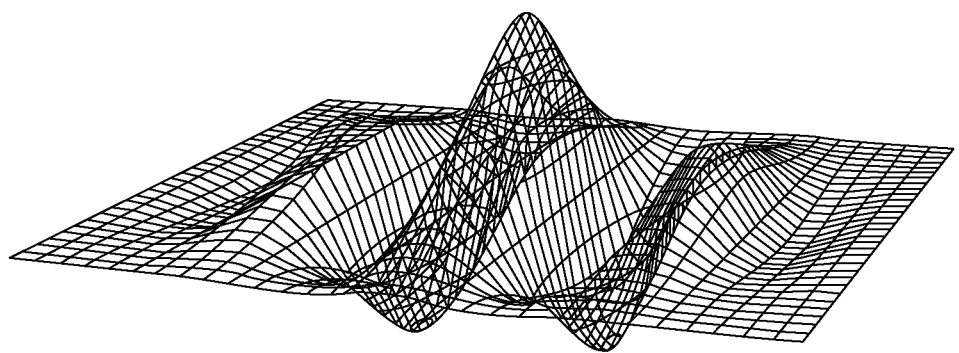
FIGS. 10A and 10B illustrate examples of a filter.
Figure 10B:
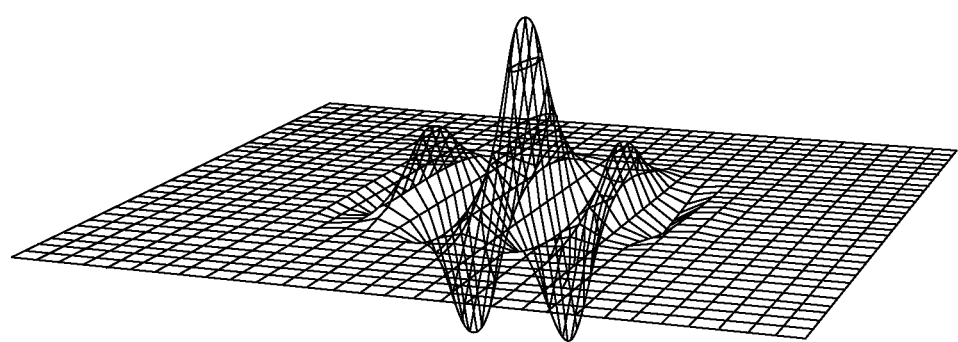

FIGS. 10A and 10B illustrate examples of Gabor filters of different frequencies. FIGS. 10A and 10B both illustrate the filters of 0-degree direction, and the filter illustrated in FIG. 10A is set to a high frequency so as to be more sensitive to a thin blood vessel. The filter illustrated in FIG. 10B is set to a low frequency so as to be more sensitive to a thicker blood vessel.

The detection unit 192 recognizes a pixel in which the output of the Gabor filter is equal to or greater than a predetermined threshold as a pixel of the blood vessel portion, and can thus extract the blood vessel.

In addition, the detection unit 192 retains the number of pixels in which the output of the Gabor filter is equal to or greater than the threshold for each of the filter frequencies, and retains the filter frequency at which the number of pixels in which the output is equal to or greater than the threshold is greatest.

A case in which the filter frequency at which the number of pixels in which the output is equal to or greater than the threshold is greatest is a frequency lower than a predetermined frequency may correspond to a case in which a thick blood vessel around the optic disc has been captured or a case in which something greater such as a trace of bleeding has been captured. In addition, a case in which the filter frequency at which the number of pixels in which the output is equal to or greater than the threshold is greatest is a frequency higher than a predetermined frequency may correspond to a case in which a thin blood vessel or a small disease such as hard exudate has been captured.

In the present exemplary embodiment, it is sufficient that the tendency of the luminance in a blood vessel area be obtained, and thus a function of detecting a blood vessel in detail is not required. It is also acceptable to detect only a blood vessel. In addition, although the Gabor filter is used as the filter, the filter is not limited thereto as long as the tendency of the frequency of a blood vessel, an affected part, or the like in the image and the tendency of the luminance difference can be obtained.

In step S803, the detection unit 192 detects the highlight point and the shadow point from the fundus image. This processing differs from the detection of the highlight point and so on in step S302 of the first exemplary embodiment in that the shadow point is detected from the blood vessel extracted in step S802. In other words, the shadow point includes the blood vessel portion included in the fundus image in the present exemplary embodiment.

As the blood vessel is set as the shadow point, even in a case in which a dark portion caused by miosis or an unexpected appearance of an eyelash takes up an unexpectedly large area, the shadow point can be set with the blood vessel portion serving as a reference. Therefore, the robustness in the image processing against a negative influence during imaging can be improved.

Specifically, the detection unit 192 acquires a histogram of pixels in which the output of the Gabor filter is equal to or greater than a predetermined threshold, and detects, as the shadow point, a pixel having a luminance value that is at the thirtieth percentile from the dark portion on the basis of the acquired histogram. In the present exemplary embodiment, there is a possibility that not only the blood vessel but also an affected part are extracted in the pixels in which the output of the Gabor filter is equal to or greater than the predetermined threshold, and thus the luminance value at the thirtieth percentile from the dark side is set as the shadow point. The shadow point is not limited to a portion at which the luminance is at the thirtieth percentile from the dark side, and a pixel with a different luminance value may instead be set as the shadow point.

In step S804, the detection unit 192 detects the tone of the fundus image with the use of the highlight point and the shadow point. The processing in step S804 is the same as the processing in step S303 of the first exemplary embodiment, and thus detailed descriptions thereof will be omitted.

In step S805, the detection unit 192 detects the contrast in the fundus image. In the contrast detection in step S304 of the first exemplary embodiment, the luminance difference between the highlight point and the shadow point, which are obtained as a result of the detection in step S302, is detected as the contrast value. However, in the present exemplary embodiment, the number of pixels in which the output of the filter is equal to or greater than a threshold as obtained in the extraction of the blood vessel in step S802 serves as the contrast value. In other words, the edge amount detected in the edge detection in the fundus image is detected as the contrast value. An image with a low contrast due to the clouding or the like of the crystalline lens results in a low output of the filter for extracting the blood vessel in step S802, and thus the number of pixels in which the output of the filter is equal to or greater than the threshold is used as the contrast value. The number of pixels in which the output of the filter is equal to or greater than the threshold may be the number of pixels in which the output of a filter among the plurality of filters described above is equal to or greater than the threshold is greatest or may be a mean value of the outputs of the plurality of filters.

In step S806, the correction unit 193 carries out the color correction of the fundus image. The processing in step S806 is the same as the processing in step S305 of the first exemplary embodiment, and thus detailed descriptions thereof will be omitted.

In step S807, the enhancement unit 194 enhances the contrast by carrying out the unsharp masking processing, as in the first exemplary embodiment.

The difference from the contrast enhancement in the first exemplary embodiment is that the filter frequency at which the number of pixels in which the output is equal to or greater than the threshold is greatest acquired in step S802 is used and that the contrast value detected in step S805 is used as the enhancement amount.

Specifically, the enhancement unit 194 determines the size of the unsharp mask (size of the processing mask) on the basis of the filter frequency at which the number of pixels in which the output is equal to or greater than the threshold is greatest acquired in step S802. Specifically, as the filter frequency is higher, the size of the unsharp mask is set smaller.

Furthermore, the enhancement unit 194 determines the enhancement amount on the basis of the contrast value detected in step S805, for example, in accordance with the characteristics illustrated in FIG. 8. In other words, the enhancement unit 194 that corresponds to an example of the correction unit enhances the contrast in the fundus image in accordance with the detected edge amount. In addition, the contrast value is higher as the detected edge amount is greater, and the enhancement degree of the contrast is smaller as the detected edge amount is greater, as illustrated in FIG. 8.

As the filter size for the contrast enhancement is determined on the basis of the frequency determined through the blood vessel extraction, the filter size for the contrast enhancement can be prevented from being set unnecessary large. As a result, the processing time can be reduced and the excessive contrast enhancement can be prevented.

According to the present exemplary embodiment, an effect similar to that of the first exemplary embodiment can be obtained. In addition, the blood vessel portion can be set as the shadow point, and thus the robustness in the image processing against a negative influence during imaging can be improved.

Third Exemplary Embodiment

A third exemplary embodiment will be described. In the present exemplary embodiment, unlike the first exemplary embodiment, the color correction algorithm of the first exemplary embodiment is carried out for each channel of RGB. The configuration of the apparatus is substantially the same as that of the first exemplary embodiment, and thus detailed descriptions thereof will be omitted.

Figure 11A:
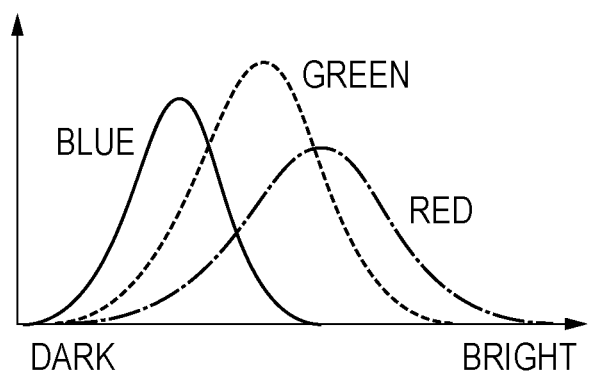
FIGS. 11A and 11B illustrate examples of color components contained in a fundus image.
Figure 11B:
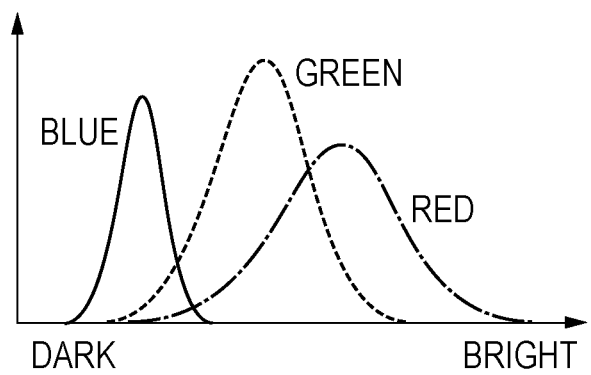

FIGS. 11A and 11B schematically illustrate examples of the histograms for the respective channels of RGB of the fundus image. FIG. 11A illustrates the histogram of the fundus image of a normal eye, and FIG. 11B illustrates the histogram of the fundus image of an eye with cataract. The horizontal axis represents the luminance, and the histograms are plotted such that the luminance is lower toward the left side of the paper plane and is higher toward the right side of the paper plane. In addition, in FIGS. 11A and 11B, the red channel is indicated by the dashed-dotted lines, the green channel is indicated by the broken lines, and the blue channel is indicated by the solid lines.

Light at a short wavelength is scattered due to the clouding, and thus the distribution range of each of the RGB channels in the fundus image of the eye with cataract is narrower than the distribution range in the fundus image of the normal eye. The blue component is scattered by the clouding at a higher rate than the other color components, and thus the luminance distribution of the blue channel in particular on the shorter wavelength side is narrow, and the luminance is low as well. With respect to the histogram illustrated in FIG. 11B, the blue tone is insufficient overall in the image, which results in an image that looks as if it is overdyed in yellow, and the visual recognizability of the fundus deteriorates.

In the present exemplary embodiment, the image processing is carried out on the fundus image with the use of the histogram illustrated in FIG. 11B.

An example of the processing procedures of the image processing unit 19 according to the third exemplary embodiment will be described with reference to FIG. 12. FIG. 12 is a flowchart illustrating an example of the flow of the image processing according to the present exemplary embodiment.

In the present exemplary embodiment, described is a case in which the image processing unit 19 carries out the image processing on a captured image that the control unit 20 has read out from the storage unit on the basis of an instruction from the operation unit 22. The control unit 20 may read out the image from an internal storage unit or an external storage unit of the fundus imaging apparatus.

In step S1201, the determination unit 191 determines an area to be analyzed by the detection unit 192. The processing in step S1201 is the same as the processing in step S301 of the first exemplary embodiment, and thus detailed descriptions thereof will be omitted.

In step S1202, the detection unit 192 detects the highlight point and the shadow point from the fundus image. The difference from the detection of the highlight point and so on in step S302 of the first exemplary embodiment is that the histogram is acquired for each of the channels in the RGB color space and the highlight point and the shadow point are detected in each of the channels.

In step S1203, the detection unit 192 detects the tone from the fundus image. The processing in each of the channels in step S1203 is the same as the processing in step S303 of the first exemplary embodiment, and thus detailed descriptions thereof will be omitted.

In step S1204, the detection unit 192 detects the contrast in the fundus image. The processing in each of the channels in step S1204 is the same as the processing in step S304 of the first exemplary embodiment, and thus detailed descriptions thereof will be omitted.

In step S1205, the correction unit 193 carries out the color correction of the fundus image. In this step, the correction unit 193 corrects the blue channel. In the present exemplary embodiment, the blue channel is corrected with the use of gamma-correction. Hereinafter, a method for obtaining $\gamma$ will be described.

(1) The target ($B^{HT}$) of the highlight point of the blue channel is obtained from the highlight point ($G^{HP}$) of the green channel through the expression (2).

$$B^{HT}T=0.6*G^{HP} \quad (2)$$

(2) If this $B^{HT}$ takes a value that is lower than the highlight point ($B^{HP}$) of the blue channel, it is determined that the correction is not necessary, and the color correction processing is not carried out. This determination is made, for example, in order to prevent the image processing for the eye with cataract from being carried out on the fundus image of an eye without cataract, and this determination may be omitted if the image processing for the eye with cataract is to be manually instructed.

(3) The correction gamma is obtained as a logarithm with a base of $B^{HT}/255$ through the expression (3).

$$\gamma = \log{_{B^{HT}/255}}(B^{HP}/255) \qquad (3)$$

The luminance value of the blue channel is corrected with the γ-value obtained as described above. In other words, the luminance value of the blue channel is raised, and the distribution range is also broadened.

The method for the correction is not limited to the above-described method, as long as the luminance value of the blue channel can be raised and the distribution range can be broadened. For example, the distribution range may be broadened so as to bring the highlight point and the shadow point of the blue channel closer to predetermined values.

In step S1206, the enhancement unit 194 carries out the contrast enhancement. The processing in step S1206 is the same as the processing in step S306 of the first exemplary embodiment, and thus detailed descriptions thereof will be omitted.

An advantage of the present exemplary embodiment over the first exemplary embodiment is that the wavelength characteristics of each of RGB can be maintained. The blue channel having a short wavelength indicates, from its wavelength characteristics, the characteristics of a surface layer of the retina as represented by a nerve fiber layer. In the meantime, the red channel having a long wavelength reflects the information on a site deeper inside the retina. Since the tone is corrected through the three-dimensional transformation in the method of the first exemplary embodiment, the difference among the RGB channels arising due to the characteristics of these wavelengths is reduced. In contrast, the correction is made for each of the channels of RGB in the method of the present exemplary embodiment, and thus the characteristics of each wavelength are maintained.

On the other hand, an advantage of the first exemplary embodiment over the present exemplary embodiment can be that, since the correction is carried out from the information on the three channels, the effect of the correction on the information rendered across the entire channels, such as a blood vessel, is strong, and the first exemplary embodiment is more effective with respect to heavier clouding.

The flow of the image processing in the third exemplary embodiment is illustrated in FIG. 12, and an additional description of the processing in each of the steps will be given. In addition, in the present exemplary embodiment, as in the first exemplary embodiment, an exemplary embodiment in which the image processing unit is provided inside the control unit 20 and the image processing is carried out on a captured image upon the operation unit 22 being operated is described.

Through the image processing described thus far, features such as a blood vessel in a fundus image whose visual recognizability is reduced due to the clouding or the like can be enhanced, and the image can be corrected to an image with a high diagnostic value. In particular, the visual recognizability can be improved while maintaining the wavelength characteristics of each of RGB, and thus an image with a higher diagnostic value can be provided.

Modifications

Although the color correction and the contrast enhancement are carried out on the fundus image in the exemplary embodiments described above, either one of the color correction and the contrast enhancement may be carried out. Even when either one of the color correction and the contrast enhancement is carried out, the effect of improving the visual recognizability of the image can be obtained.

In addition, although a typical eye without clouding is measured in advance and the information on that eye is retained as the transformation target of the color correction in the exemplary embodiments described above, the present invention is not limited thereto. For example, when a measurement apparatus or an imaging mode changes, the color characteristics also change. Therefore, a target that is different for a different measurement apparatus or imaging mode may be retained, and the target may be switched. Furthermore, the target may be changed in accordance with the information on the race, the color adjustment information of an output image, and so on.

Furthermore, although the image processing on the color fundus image is illustrated as an example in the exemplary embodiments described above, the image processing may also be applied to a color anterior eye portion image. In addition, the image processing described above may be applied to a black and white fundus image or anterior eye portion image.

In addition, image processing that is different from the image processing described above may further be included. The different image processing can be image processing that, for example, does not include the rotational transformation. The examiner may be able to select whether to carry out the image processing described above corresponding to the clouding or to carry out the different image processing through the operation unit 22, and the image processing unit 19 may carry out the selected image processing on the fundus image or the like.

Although the histogram of the blue component is changed in the exemplary embodiments described above, the color correction may be carried out by, instead of changing the histogram of the blue component, changing the histograms of the red component and of the green component such that the ratio of the blue component increases against the ratios of the red component and of the green component.

Thus far, the exemplary embodiments have been described in detail, but the present invention can also be implemented, for example, in the form of a system, an apparatus, a method, a program, a recording medium (storage medium), or the like. Specifically, the present invention may be applied to a system constituted by a plurality of devices (e.g., a host computer, an interface device, an imaging device, a web application, etc.) or may be applied to an apparatus constituted by a single device.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that these exemplary embodiments are not seen to be limiting. The scope of the following claims is to be accorded the broadest interpretation so as to encompass all such modifications and equivalent structures and functions.

This application claims the benefit of Japanese Patent Application No. 2015-016745 filed Jan. 30, 2015, which is hereby incorporated by reference herein in its entirety.

What is claimed is:

1. An ophthalmologic apparatus, comprising:
   an image acquisition unit configured to acquire a fundus image of an eye to be examined; and
   a correction unit configured to correct the fundus image in accordance with a degree of clouding of the eye such that, among color components contained in the fundus image, a ratio of a blue component in the fundus image increases against a red component and a green component.

2. The ophthalmologic apparatus according to claim 1, further comprising:
   a detection unit configured to detect a highlight point and a shadow point from a luminance distribution of the fundus image,
   wherein the correction unit causes, among the color components contained in the fundus image, the ratio of the blue component in the fundus image to increase against the red component and the green component, so that an angle formed by a straight line connecting the highlight point and the shadow point in the color space and a predetermined coordinate axis defining the color space approaches a predetermined angle.

3. The ophthalmologic apparatus according to claim 2, wherein the predetermined angle is an angle formed by a straight line connecting a highlight point and a shadow point obtained from a luminance distribution of a fundus image of an eye with clouding that is less than a threshold and the predetermined coordinate axis.

4. The ophthalmologic apparatus according to claim 3, wherein the detection unit detects a luminance difference between the highlight point and the shadow point, and wherein the correction unit enhances a contrast in the fundus image in accordance with the luminance difference.

5. The ophthalmologic apparatus according to claim 4, wherein the correction unit reduces an enhancement degree of the contrast as the luminance difference is greater.

6. The ophthalmologic apparatus according to claim 2, wherein the detection unit detects the highlight point and the shadow point from the luminance distribution of a region excluding an optic disc in the fundus image.

7. The ophthalmologic apparatus according to claim 6, wherein the detection unit detects a luminance difference between the highlight point and the shadow point, and wherein the correction unit enhances a contrast in the fundus image in accordance with the luminance difference.

8. The ophthalmologic apparatus according to claim 7, wherein the correction unit reduces an enhancement degree of the contrast as the luminance difference is greater.

9. The ophthalmologic apparatus according to claim 2, wherein the detection unit detects a luminance difference between the highlight point and the shadow point, and wherein the correction unit enhances a contrast in the fundus image in accordance with the luminance difference.

10. The ophthalmologic apparatus according to claim 9, wherein the correction unit reduces an enhancement degree of the contrast as the luminance difference is greater.

11. The ophthalmologic apparatus according to claim 2, wherein the shadow point includes a blood vessel portion included in the fundus image.

12. The ophthalmologic apparatus according to claim 1, wherein the detection unit carries out an edge detection on the fundus image, and
    wherein the correction unit enhances a contrast in the fundus image in accordance with the detected edge amount.

13. The ophthalmologic apparatus according to claim 12, wherein the correction unit reduces an enhancement degree of the contrast as the edge amount is greater.

14. An image processing method, comprising:
    acquiring a fundus image of an eye to be examined; and
    correcting the fundus image in accordance with a degree of clouding of the eye such that, among color components contained in the fundus image, a ratio of a blue component in the fundus image increases against a red component and a green component.

15. A non-transitory storage medium storing a program that causes a computer to execute each step of the image processing method according to claim 14.

* * * * *